United States Patent [19]
Loev et al.

[11] 4,354,027
[45] Oct. 12, 1982

[54] TRIAZOLOQUINOXALIN-4-ONES

[75] Inventors: Bernard Loev, Scarsdale, N.Y.; John T. Suh, Greenwich, Conn.; Bruce E. Williams, Cottage Grove, Minn.; Vassil St. Georgiev, New Rochelle, N.Y.

[73] Assignee: USV Pharmaceutical Corporation, Tarrytown, N.Y.

[21] Appl. No.: 151,220

[22] Filed: May 19, 1980
(Under 37 CFR 1.47)

[51] Int. Cl.³ ............... C07D 487/04; C07D 241/44; C07D 491/14; A61K 31/495
[52] U.S. Cl. .................................. 544/346; 544/343; 544/354; 424/250
[58] Field of Search ............... 424/250; 544/346, 343

[56] References Cited
PUBLICATIONS

"Kingzetl's Chemical Encyclopaedia", 9th Edition p. 18.
Condensed Chemical Dictionary 8th Edition, p. 16.
Hackh's Chemical Dictionary, 4th Ed. (1969) p. 6.
Koshel et al., Chem. Abs. 73, 120589c (1970).
Saikuchi et al., Chem. Abs. 59, 1634h (1962).

Primary Examiner—Mark L. Berch

[57] ABSTRACT

New substituted triazoloquinoxalin-4-ones are described as well as the use thereof as anti-hypertensive agents.

7 Claims, No Drawings

TRIAZOLOQUINOXALIN-4-ONES

This invention relates to new anti-hypertensive agents and more particularly to certain new substituted triazoloquinoxalin-4-ones possessing useful anti-hypertensive activity.

The substituted triazoloquinoxalin-4-ones of this invention are new compounds not previously described in the literature and show significant anti-hypertensive activity as shown in the standard tests used for evaluation of such activity. Unsubstituted but otherwise comparable triazoloquinoxalines have some anti-hypertensive activity but also have a significant toxicity which mitigates against use of such compounds in therapy. The present substituted compounds are free of toxicity even at substantially high dosage levels.

Triazoloquinoxalin-4-ones which are unsubstituted in the benzenoid moiety are described in the literature, e.g., 4H-1,2,4-triazolo(5,3-a)quinoxalin-4-one and the corresponding 1-methyl compound in Chem. Abst. 73, 120589c and the corresponding 1,5-dimethyl compound in Chem. Abst. 59, 1634h.

The new triazoloquinoxalines of this invention are of the following formula:

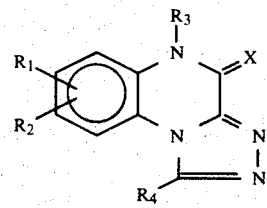

Formula I wherein,
X is S or O;
each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylamino, alkanoylamino, carbalkoxyamino, methanesulfonyl, carboxy, carbalkoxy, or trihalomethyl, or taken together, methylenedioxy with the proviso that at least one of $R_1$ and $R_2$ is other than H; and each of $R_3$ and $R_4$ is hydrogen, alkyl, alkenyl, alkynyl, aryl, acyl, aralkyl, cycloalkyl, cycloalkyl-$CH_2$-, alkanoyl, or carbalkoxy;
and acid addition salts thereof.
The total number of carbon atoms in each such hydrocarbyl substituent can range up to about 10.

The preferred compounds are those in which the hydrocarbyl radicals contain up to about 7 carbon atoms when aliphatic and up to 10 carbon atoms when aromatic, e.g., phenyl, tolyl and naphthyl.

The particularly preferred compounds of the invention are those in which X is oxygen, that is the triazoloquinoxalin-4-ones.

The new compounds of the invention can be prepared by art-recognized procedures from known starting compounds. For example, the following procedure can be employed:

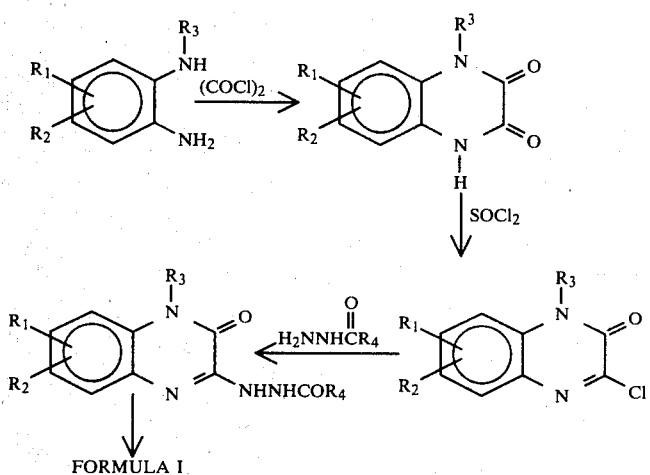

FORMULA I

Substituents $R_1$ to $R_4$ can be added after formation of the basic ring structures by known substitution reactions, or conversion of substituents such as reduction of nitro to form amino. The substitution reactions mentioned include, for example, alkylation and acylation by known procedures.

Substituents on the present new compounds which are reactive and could interfere with ring closure reactions are best introduced by subsequent reactions known to the art such as reduction of nitro to amino, or hydrolysis of cyano to carboxamide or carboxy groups; alternatively, such reactive groups can be protected as by, for example, acylation of an amino group, followed by hydrolysis after ring closure.

Using the procedures described, a wide variety of heterocyclic compounds can be prepared, as follows:

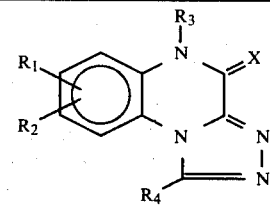

| $R_1$ | $R_2$ | X | $R_3$ | $R_4$ |
|---|---|---|---|---|
| $OC_3H_7$ | H | O | $CH_3$ | $COCH_3$ |
| $CH_3$ | H | O | $C_2H_5$ | $n\text{-}C_3H_7$ |
| $CH_3$ | $CH_3$ | O | $CH_3$ | $i\text{-}C_3H_7$ |

-continued

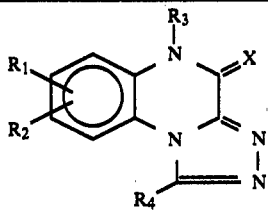

| R1 | R2 | X | R3 | R4 |
|---|---|---|---|---|
| Cl | H | S | H | $C_6H_5$ |
| $OCH_3$ | H | O | $C_7H_{15}$ | $C_6H_5CH_2-$ |
| $C_6H_5$ | H | O | $C_6H_{11}$ | $CH_3C_5H_4$ |
| $CF_3$ | $CH_3$ | O | $C_3H_7$ | $C_3H_7CO$ |
| $OC_3H_5$ | H | S | $C_6H_5CH_2$ | $COOCH_3$ |
| $OC_6H_5$ | H | O | $C_6H_5$ | $C_4H_9CO$ |
| $OCH_3$ | H | O | $C_{10}H_7$ | H |
| OH | $CH_3$ | O | $C_3H_3$ | H |
| $C_4H_9$ | OH | O | $C_6H_5CO$ | H |
| $CH_2OH$ | H | O | H | $C_4H_7$ |
| $NH_2$ | $OCH_3$ | O | H | $C_4H_9$ |
| $NHCH_3$ | H | O | $CH_3$ | H |
| SH | H | O | $C_3H_7$ | H |
| $SC_3H_7$ | H | O | $C_2H_5$ | H |
| $C_4H_7$ | $OCH_3$ | O | $C_7H_{15}$ | H |
| $NO_2$ | H | O | $CH_3$ | $CH_3CO$ |
| $C_6H_5CH_2O$ | H | O | H | $CH_3$ |
| $OCF_3$ | H | O | H | $CH_3CO$ |
| $C_2H_4NH_2$ | H | O | H | H |
| $CF_3$ | H | O | $CH_3$ | H |
| $OCH_3$ | $OCH_3$ | O | $CH_3$ | H |
| $OCH_3$ | $CF_3$ | O | $CH_3$ | H |

The compounds of this invention are characterized by the presence of at least one substituent on the benzenoid moiety, preferably lower alkoxy. Without the benzenoid substituent, the said compounds have a substantial toxicity as evidenced by a comparison of 8-methoxy-5-methyl-1-propyl-4H-1,2,4-triazolo(4,3-a)quinoxalin-4-one with the corresponding compound without the 8-methoxy group, i.e., 5-methyl-1-propyl-4H-1,2,4-triazolo(4,3-a)-quinoxalin-4-one. In toxicity determinations, the latter compound showed an $LD_{50}$ of 80 mg./kg. whereas the former evidenced no toxicity even at a level of 320 mg./kg. in rats. Both compounds were tested for anti-hypertensive activity in the spontaneously hypertensive rat screen and were effective orally at 10 mg./kg.

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-hypertensive agents. These compounds also demonstrate significant anti-allergic activity, acting via inhibition of mediator release. The compounds are active orally in the passive cutaneous anaphylaxis (PCA) screen; and/or inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

8-Methoxy-5-methyl-1-propyl-4H-1,2,4-triazolo(4,3-a)quinoxalin-4-one

A mixture of 6-methoxy-1-methyl-3-(2'-butanoyldiazanyl)-1H-quinoxalin-2-one (10.9 g., 27.5 mmol) and phenol (27.3 g.) was heated at 180° for 3.5 hours and allowed to cool to room temperature. The mixture was diluted with 50 ml. of ether and the resulting solid collected by filtration and washed with ether. The material was recrystallized from acetonitrile, collected by filtration, and dried under high vacuum overnight to give 7.6 g. of 8-methoxy-5-methyl-1-propyl-4H-1,2,4-triazolo(4,3-a)quinoxalin-2-one, m.p. 219°–220°.

EXAMPLE 2

8-Chloro-5-methyl-1-propyl-4H-1,2,4-triazolo(4,3-a)quinoxalin-4-one

A mixture of 6-chloro-1-methyl-3-(2'-butanoyldiazanyl)-1H-quinoxalin-2-one (10.0 g., 33.9 mmol) and phenol (25.0 g.) was heated at 180° for 3.5 hours and then allowed to cool to room temperature. The mixture was diluted with 50 mo. of ether and the resulting solid collected by filtration and washed with ether. The material was recrystallized from acetonitrile, collected by filtration, and dried under vacuum for 3 days to give 4.8 g. of 8-chloro-5-methyl-1-propyl-4H-1,2,4-triazolo(4,3-a)quinoxalin-4-one, m.p. 265°–266°.

EXAMPLE 3

5-Methyl-1-propyl-8-trifluoromethyl-4H-1,2,4-triazolo(4,3-a)quinoxalin-4-one A mixture of 1-methyl-6-trifluoromethyl-3-(2'-butanoyldiazanyl)-1H-quinoxalin-2-one (8.4 g., 25.6 mmol) and phenol (21.0 g.) was heated at 180° for 3.5 hours and allowed to cool to room temperature. The mixture was diluted with 50 ml. of ether and the resulting solid collected by filtration, and washed with ether. The material was recrystallized from acetonitrile, and dried under high vacuum overnight to give 3.8 g. of 5-methyl-1-propyl-8-trifluoromethyl-4H-1,2,4-triazolo(4,3-a)quinoxalin-4-one, m.p. 257°–258°.

EXAMPLE 4

A.

1-Methyl-6-methoxy-1,4-dihydroquinoxalin-2,3-dione

2-Methylamino-5-methoxyaniline dihydrochloride (0.256 mol) is neutralized with sodium hydroxide (22 g., 0.5 mol) in 80 ml. of water. The free amine is extracted into 300 ml. of xylene, the solution dried over magnesium sulfate, and filtered. This solution is then added over 50 min. to a solution of oxalyl chloride (39 g., 0.307 mol) in 300 ml. of xylene held at 75°–90° C. After addition is complete, the resulting solution is heated to a bath temperature of 155° and then allowed to cool to room temperature. The flask is cooled to 0° and the gray precipitate collected by vacuum filtration. The solid product is then dried under high vacuum at 160° for two hours.

B.

3-Hydrazino-1-methyl-6-methoxy-1H-quinoxalin-2-one

Thionyl chloride (22.2 g., 0.186 mol) is added to a suspension of the paragraph A product (0.155 mol) in a solution of 7.5 ml. of DMF and 760 ml. of toluene and heated to reflux for 70 min. The solution is filtered, cooled to room temperature, and the solvent removed on the rotary evaporator. Then a solution of hydrazine hydrate (19 g., 0.38 mol) in 750 ml. of ethanol is added and the mixture heated to reflux for 2 hours. The solvent is removed on the rotary evaporator and the resulting solid washed with water and air dried. The material is recrystallized from 900 ml. of methanol to give purified product.

C.

1-Methyl-3-(2'-benzoyldiazanyl)-6-methoxy-1H-quinoxalin-2-one

Benzoyl chloride (4.44 g., 31.6 mmol) is added dropwise to a solution of the paragraph B product (26.3 mmol) and triethylamine (3.19 g., 31.6 mmol) in 300 ml. of dioxane and stirred at room temperature for 20 hours. The dioxane is removed under vacuum and the residue washed with water and dried under vacuum to give crude product which was used without further purification.

D.

1-Phenyl-5-methyl-8-methoxy-4H-1,2,4-triazaol(4,3-a)quinoxalin-4-one

A mixture of the paragraph C product (27.2 mmol) and phenol (20 g.) is heated at 180° for 3.5 hours, and then allowed to cool to room temperature and stand overnight. The mixture is diluted with ether and the resulting solid collected by filtration and washed with ether. The material is then recrystallized from acetonitrile and the crystals collected by filtration, washed with ether and dried under vacuum at 80° to give purified product.

EXAMPLE 5

A.

1-Methyl-3-(2'-pentanoyldiazanyl)-6-chloro-1H-quinoxalin-2-one

Pentanoyl chloride (52.6 mmol) is added dropwise to a solution of 3-hydrazino-1-methyl-6-chloro-1H-quinoxalin-2-one (43.8 mmol) and triethylamine (52.6 mmol) in 500 ml. of dioxane and stirred at room temperature for 2 hours. The dioxane is removed under vacuum and the residue washed with water and ether, filtered and dried under high vacuum at 65° for 3 hours to give crude product.

B.

1-Butyl-5-methyl-8-chloro-4H-1,2,4-triazolo(4,3-a)quinoxalin-4-one

A mixture of the paragraph A product (23 mmol) and phenol (16 g.) is heated at 180° for 3.5 hours and then allowed to cool to room temperature and stand overnight. The mixture is diluted with ether and the resulting solid collected by filtration and washed with ether. The material is then recrystallized from 150 ml. of acetonitrile and the crystals collected by filtration, washed with ether, and dried under high vacuum at 80° for 18 hours to give the product.

EXAMPLE 6

A.

1-Methyl-3-(2'-propanoyldiazanyl)-6-methoxy-1H-quinoxalin-2-one

Propionyl chloride (2.63 g., 28.4 mmol) is added dropwise to a solution of 3-hydrazino-1-methyl-6-methoxy-1H-quinoxalin-2-one (4.5 g., 23.7 mmol) and triethylamine (2.87 g., 28.4 mmol) in 250 ml. of dioxane and stirred at room temperature for four days. The dioxane is then removed under vacuum and the residue washed with water, filtered, and dried at 80° C. under high vacuum. The material is then recrystallized from ethanol, filtered and dried at 80° under high vacuum overnight to yield purified product.

B.
1-Ethyl-5-methyl-4H-1,2,4-triazolo(4,3-a)-quinoxalin-4-one

A mixture of the paragraph A product (39.8 mmol) and phenol (24.5 g.) is heated at 180° for 3 hours and then allowed to cool to room temperature and stand overnight. The mixture is diluted with ether and the resulting solid collected by filtration and washed with ether. The material is then recrystallized from 750 ml. of ethanol and the crystals collected by filtration, washed with ether and dried under high vacuum at 60° to give purified product.

EXAMPLE 7
A.
1-Methyl-3-(2'-[3-methylbutanoyl]diazanyl)-6-trifluoromethyl-1H-quinoxalin-2-one To a solution of 3-hydrazino-1-methyl-6-trifluoromethyl-1H-quinoxalin-2-one (10.0 g., 52.6 mmol) and triethylamine (6.38 g., 63.2 mmol) in 500 ml. of dioxane is added dropwise 3-methylbutanoyl chloride (7.62 g., 65.2 mmol) and the mixture stirred at room temperature for 20 hours. The dioxane is then removed under vacuum and the residue washed with water and ether, filtered and dried under vacuum to give the product.

B.
1-(2-Methylpropyl)-5-methyl-8-methoxy-4H-1,2,4-triazolo(4,3-a)quinoxalin-4-one A mixture of the paragraph A product (24.8 mmol) and phenol (17 g.) is heated at 180° for 3.5 hours and then allowed to cool to room temperature and stand overnight. The mixture is diluted with ether and the resulting solid collected by filtration and washed with ether. The material is recrystallized from 100 ml. of 2-propanol and the crystals collected by filtration and washed with ether. The white crystals were dried under high vacuum at 80° for 7 hours to yield the product.

EXAMPLE 8
A.
1-Methyl-3-(2'-(2-methylpropanoyl)diazanyl)-6-methoxy-1H-quinoxalin-2-one To a solution of 3-hydrazino-1-methyl-6-methoxy-1H-quinoxalin-2-one (46.2 mmol) and triethylamine (5.6 g., 55.4 mmol) in 500 ml. of dioxane was added dropwise 2-methylpropanoyl chloride (5.91 g., 55.4 mmol) and the mixture stirred at room temperature for 1.5 hours. The dioxane was then removed under vacuum and the residue washed with water and ether, filtered, and dried at 65° for three hours to yield crude product.

B.
1-(1-Methylethyl)-5-methyl-8-methoxy-4H-1,2,4-triazolo(4,3-a)-quinoxalin-4-one A mixture of the paragraph A product (25.7 mmol) and phenol (17 g.) is heated at 180° for 3.5 hours and then allowed to cool to room temperature and stand overnight. The mixture is diluted with ether and the resulting solid collected by filtration and washed with ether. The material is then recrystallized from 200 ml. of ethanol and the crystals collected by filtration, and dried under high vacuum at 80° for 18 hours to give purified product.

EXAMPLE 9
A.
1-Methyl-3-(2'-cyclopropanoyldiazanyl)-6-methoxy-1H-quinoxalin-2-one Cyclopropylcarboxylic acid chloride (6.60 g., 6.32 mmol) is added dropwise to a solution of 3-hydrazino-1-methyl-6-methoxy-1H-quinoxalin-2-one (52.6 mmol) and triethylamine (6.38 g., 63.2 mmol) in 500 ml. of dioxane and the mixture stirred at room temperature for 20 hours. The dioxane is then removed under vacuum and the residue washed with water, filtered, and dried under vacuum to give a crude yield of 12.8 g. (95%). A 4.8 g. sample of this material is recrystallized from 100 ml. of acetonitrile to obtain purified product.

B.
1-Cyclopropyl-5-methyl-8-methoxy-4H-1,2,4-triazolo(4,3-a) quinoxalin-4-one A mixture of the paragraph A product (31.0 mmol) and phenol (20 g.) is heated at 180° for 3.5 hours and then allowed to cool to room temperature and stand overnight. The mixture is diluted with ether and the resulting solid collected by filtration and washed with ether to give 5.5 g. of crude product, which is recrystallized from 275 ml. of ethanol to obtain purified product.

What is claimed is:

1. An anti-hypertensive compound of the formula

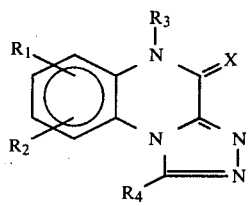

wherein
X is S or O;
each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, nitro, amino, alkylamino, alkanoylamino, carbalkoxyamino, methanesulfonyl, carboxy, carbalkoxy or trihalomethyl, or taken together, methylenedioxy, with the proviso that at least one of $R_1$ and $R_2$ is other than H;
$R_3$ is hydrogen, alkyl, alkenyl, alkynyl, aryl, aralkyl, cycloalkyl or cycloalkyl-$CH_2$-;
$R_4$ is hydrogen, alkyl, alkenyl, alkynyl, aryl, aralkyl, cycloalkyl, cycloalkyl-$CH_2$-, alkanoyl, or carbalkoxy;
wherein the hydrocarbyl groups of $R_1$, $R_2$, $R_3$ and $R_4$ independently contain up to 7 carbon atoms when aliphatic and up to 10 carbon atoms when cycloalkyl or aromatic; and pharmaceutically acceptable acid addition salts thereof.

2. An anti-hypertensive compound of the formula

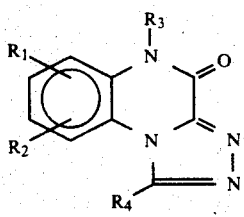

wherein
each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, nitro, amino, alkylamino, alkanoylamino, carbalkoxyamino, methanesulfonyl, carboxy, carbalkoxy or trihalomethyl, or taken together, methylenedioxy, with the proviso that at least one of $R_1$ and $R_2$ is other than H;

$R_3$ is hydrogen, alkyl, alkenyl, alkynyl, aryl, aralkyl, cycloalkyl or cycloalkyl-$CH_2$-;

$R_4$ is hydrogen, alkyl, alkenyl, alkynyl, aryl, aralkyl, cycloalkyl, cycloalkyl-$CH_2$-, alkanoyl, or carbalkoxy;

wherein the hydrocarbyl groups of $R_1$, $R_2$, $R_3$ and $R_4$ independently contain up to 7 carbon atoms when aliphatic and up to 10 carbon atoms when cycloalkyl or aromatic; and pharmaceutically acceptable acid addition salts thereof.

3. 8-Methoxy-5-methyl-1-propyl-4-1,2,4-triazolo-(4,3-a)quinoxalin-4-one and its pharmaceutically acceptable acid addition salts.

4. 8-Trifluoromethyl-5-methyl-1-propyl-4H-1,2,4-triazolo(4,3-a)quinoxalin-4-one.

5. 8-Chloro-5-methyl-1-propyl-4H-1,2,4-triazolo-(4,3-a)quinoxalin-4-one.

6. A pharmaceutically acceptable acid addition salt of the compound of claim 3.

7. A hydrochloride salt of the compound of claim 3.